United States Patent [19]
Herweck et al.

[11] Patent Number: 5,192,310
[45] Date of Patent: Mar. 9, 1993

[54] SELF-SEALING IMPLANTABLE VASCULAR GRAFT

[75] Inventors: Steve A. Herweck, Nashua; Theodore Karwoski, Hollis; Paul Martakos, Pelham, all of N.H.

[73] Assignee: Atrium Medical Corporation, Hollis, N.H.

[21] Appl. No.: 760,718

[22] Filed: Sep. 16, 1991

[51] Int. Cl.⁵ .............................................. A61F 2/04
[52] U.S. Cl. ........................................ 623/1; 623/11; 623/12
[58] Field of Search ................................ 623/1, 11, 12

[56] References Cited

U.S. PATENT DOCUMENTS 4,619,641 10/1986 Schanzer .................................. 604/8

Primary Examiner—David Isabella
Assistant Examiner—Debra S. Brittingham
Attorney, Agent, or Firm—Lahive & Cockfield

[57] ABSTRACT

An implantable self-sealing vascular graft device comprises an implantable tubular body defining a primary lumen and at least one secondary lumen, the lumina sharing a common side wall. The primary lumen is adapted for attachment to the vascular system of the patient to accommodate blood flow therethrough. A non-biodegradable elastomeric material disposed in the secondary lumen permits repeated self-sealing penetrations of a cannula through the elastomeric material and into the primary lumen. A method for repeatedly accessing a patient's vascular system by implanting in the patient the disclosed structure and accessing a patient's vascular system by passing a cannula through the secondary lumen, the common side wall, and into the primary lumen is also disclosed.

11 Claims, 3 Drawing Sheets

SELF-SEALING IMPLANTABLE VASCULAR GRAFT

BACKGROUND OF THE INVENTION

One type of implantable device is a synthetic vascular graft such as is commonly used to replace damaged or dysfunctional arterial or venous pathways, for example at the site of an aneurysm or occlusion. Bypass grafts are often used to divert blood flow around damaged regions to restore blood flow. Another use of vascular prostheses is for creating a bypass shunt between an artery and vein, specifically for multiple needle access, such as is required for hemodialysis treatments. Following multiple percutaneous invasions into a vein, the vein may either collapse along the puncture track or become aneurysmal, leaky or fill with clot, causing significant risk of pulmonary embolization. Vascular prostheses have been used for many years as an alternative to patients' own veins for vascular access during hemodialysis.

Materials reach has led to the development of some synthetic materials for use in vascular prostheses. One example is polytetrafluoroethylene (PTFE), a porous organic material which can be expanded or stretched to a specific length and thickness. When thus expanded, the material consists of a network of interrelated nodes and fibrils. The diameters of the fibrils vary depending upon the conditions and rate at which the PTFE is stretched. An advantage of PTFE is that the diameters of the fibrils can be made much smaller than the diameters of fibers of knitted or woven fabrics which have been used for vascular prostheses. Moreover, the pore diameter and porosity of PTFE tubing can be adjusted to reduce the occurrence of thrombosis associated with vascular prostheses.

One drawback of PTFE tubing, however is that because of the relative elasticity of porous PTFE tubing, it is difficult to elicit natural occlusion of suture holes in vascular prostheses made from expanded PTFE tubing. As a result, blood cannot be withdrawn from a PTFE vascular graft until the graft has become surrounded by fibrotic tissue. This generally occurs within a minimum of 14 days after surgery.

Other materials which have been used to form prosthetic vascular grafts include autologous saphenous vein, Dacron ® brand polyester fiber or other synthetic polyester fiber, modified bovine or carotid xenograft and human umbilical vein. None of these materials, however, overcomes the problems associated with early puncture of the graft.

Schanzer in U.S. Pat. No. 4,619,641 describes a two-piece coaxial double lumen arteriovenous graft. The Schanzer graft consists of an outer tube positioned over an inner tube, the space between being filled with a self-sealing adhesive. The configuration of this coaxial tube greatly increases the girth of the graft, and limits the flexibility of the lumen which conducts blood flow.

It is, therefore, an object of the invention to provide a vascular graft having a self-sealing capability. It is another object of the invention to provide such a graft that is easily manufactured.

SUMMARY OF THE INVENTION

The present invention features a self-sealing implantable prosthetic device for connection to a fluid flow pathway of a patient. The device comprises a tubular body adapted for attachment to the fluid flow pathway. The body defines a primary lumen for accommodating fluid flow therethrough and a secondary lumen partially circumscribing the primary lumen. The lumina share a common side wall. A non-biodegradeable elastomeric material is disposed in the secondary lumen. This permits repeated self-sealing penetrations by a cannula through the secondary lumen, the common side wall, and into the primary lumen.

It is a significant feature of the invention, that the secondary lumen partially but not totally circumscribes the primary lumen. This provides a single piece unitary construction prosthetic device.

In a preferred embodiment, the present prosthetic device is made from stretched and/or expanded polytetrafluoroethylene (PTFE). Stretched and/or expanded PTFE is made up of a network of nodes and fibrils which endow the PTFE with porosity. The network of nodes and fibrils created during the manufacture of tubing from PTFE results in a semi-permeable membrane having a permeability determined by the porosity of the PTFE material.

A method for repeatedly accessing a patient's vascular system is also the subject of the present invention. The method includes the steps of implanting in the patient a structure constructed in accordance with the invention and accessing the patient's vascular system by passing a cannula through the second lumen, the common side wall, and into the first lumen of the structure.

The present device and method have several advantages, including more flexibility than vascular graft structures having a two-piece coaxial design. The presence of a polymer material completely surrounding the graft can inhibit blood flow through the graft lumen, and increase the rigidity of the grafts. The present structures provide grafts which more clearly approximate the behavior of naturally occurring veins or arteries.

BRIEF DESCRIPTION OF THE DRAWINGS

The invention will be more fully appreciated by reference to the following detailed description in conjunction with the attached drawing in which like reference numbers refer to like elements throughout the several views.

DETAILED DESCRIPTION OF THE INVENTION

Figure 1:
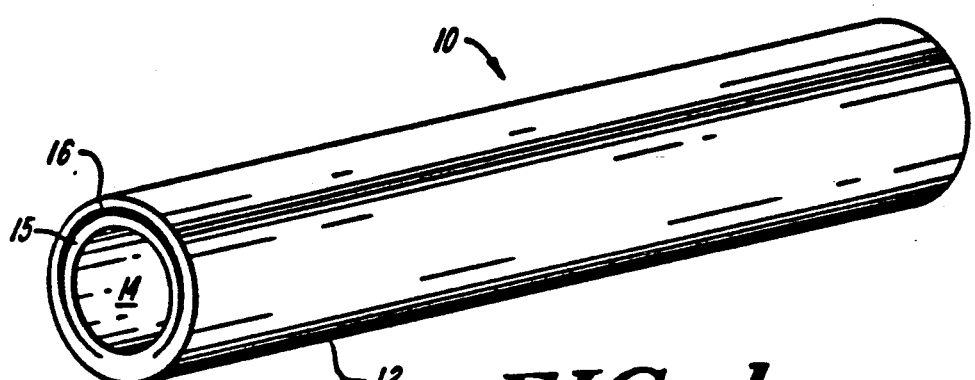
FIG. 1 is a schematic perspective view of a self-sealing vascular tubular structure.

The invention relates to an implantable self-sealing tubular device comprising at least two lumina. The device defines a primary lumen adapted for blood flow therethrough and at least one secondary lumen which contains a non-biodegradable elastomeric material, and which shares a common side wall with the primary lumen.

The device of the invention can be used as a prosthetic vein, artery, pseudo-organ, or other similar anatomical structure. In preferred embodiment, the prosthesis comprises a vascular graft. The device is implanted into the patient's arterial or venous system so that blood is established through the primary lumen.

The tube structures of the invention can be manufactured from any suitable biocompatible material that can be arranged to form a microporous structure. Polymeric materials which are useful for this purpose include, for example, either expanded or unexpanded polytetrafluoroethylene (PTFE), Dacron® brand polyester, and other synthetic polyester fibers such as mandrel spun polyurethane and silicone elastomeric fibers. Also, copolymeric materials such as described in U.S. Pat. Nos. 4,187,390 and 4,973,609 can be utilized. These are materials made up of more than one type of monomer and have advantages, as described in the cited patents, in some applications. The structures can also be formed by extrusion, form molding, or weaving using techniques well known in the art.

In a preferred embodiment, the inventive prosthesis is manufactured by paste forming and rapidly stretching and/or expanding highly crystalline, unsintered, polytetrafluoroethylene. Paste forming by extrusion of PTFE is well-known in the art. Generally, the steps in paste-forming include mixing the resin with a lubricant, such as odorless mineral spirits, and then forming the resin by extrusion into shaped articles. The lubricant is removed from the extruded article by drying, following which the article is sintered by its being heated above its crystalline melting point of approximately 327° C. The sintered, unexpanded, article is a relatively impermeable product. To achieve a greater degree of permeability in the finished product, however, the prostheses of the invention can be further treated prior to sintering.

Paste-formed, dried, unsintered, shapes can be further treated by expanding and/or stretching them in one or more directions under certain conditions so that they become porous yet retain their strength. Such stretching and expansion with increased strength occurs with certain preferred tetrafluoroethylene resins, e.g., PTFE. The porosity of the material is affected by the temperature and rate at which it is stretched and expanded. A method for manufacturing porous PTFE tubing appropriate for use in the present invention is described in detail, for example, in U.S. Pat. No. 3,953,566, and U.S. Pat. No. 4,973,609 the teachings of both of which are hereby incorporated by reference herein.

Stretched and expanded PTFE is characterized by a microstructure of nodes interconnected by small fibrils. The space between the nodes and the number of fibrils is controlled by changes in the temperature and rate of stretching and expansion of the PTFE, to produce tubing having predetermined porosity and flex qualities. For example, products which are stretched and expanded at high temperatures and high rates have a more homogeneous structure, i.e., they have smaller, more closely spaced nodes, which nodes are interconnected with a greater number of fibrils. While the resulting structure is stronger than products stretched and expanded at lower temperatures and rates, the porosity is also reduced. Thus, by controlling these two factors, it is possible t o construct a series of tube structures having a range of porosity within a desirable range of strength.

Tube structures manufactured as described above begin to lose their crystallites and the crystallinity decreases above this temperature. This is accompanied by a concomitant increase in the amorphous content of the polymer. Amorphous regions within the crystalline structure greatly inhibit slippage along the crystalline axis of the crystallite and lock fibrils and crystallites so that they resist slippage under stress. Heat treatment may be considered to be, therefore, an amorphous locking process, which results in an increase in the amorphous content and of the strength of the treated structure. Heat treatment above 327° C. has been found to cause a two-fold increase in the strength of PTFE is approximately 345° C., heat treatment is even more effective. Similar results can be achieved at lower temperatures if expose time is accordingly increased. The optimum heat treating temperature is generally in the range of from about 350° C. to about 370° C., with heating periods in the range of from about five seconds to about one hour. Other factors upon which the strength the polymer matrix is dependent upon include the strength of the extruded material before expansion, the degree of crystallinity of the polymer, the rate and temperature at which the expansion is performed, and amorphous locking.

Other paste-forming techniques can be used to form the present tube structures. Due to the physiological properties of the vascular system, it is important for the tube structures to be gas permeable, or selectively gas permeable, to permit oxygen-carbon dioxide exchange. However, even gas impermeable tube structures may be useful as vascular grafts in certain regions.

The secondary lumen is fulled with a non-biodegradable elastomer which self-compresses after puncture by a cannula or needle to seal the puncture site. Elastomeric materials which are useful for this purpose include elastomeric polymers and copolymers, including silicone rubbers, polyurethanes, and polyethers. Various fluoropolymers are suitable as well.

The present device is shown in one embodiment in FIG. 1. The device shown is a self-sealing vascular tubular structure 10 formed of a body 12. The body 12 defines lumina 14 and 18 which share common side wall 15. Disposed in the lumen 18 is a self-sealing elastomeric material 16.

Figure 2:
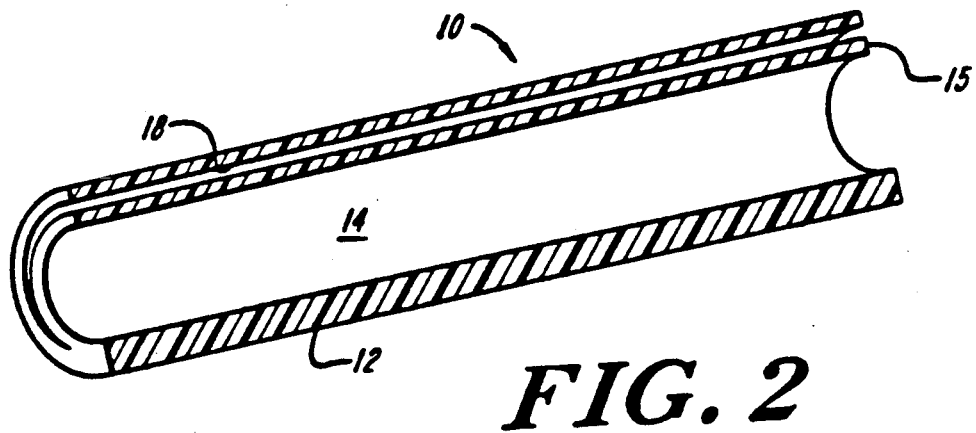
FIG. 2 is a cross-sectional view taken along line 2—2 of FIG. 1.

FIG. 2 is a cross-sectional view of the structure 10 in which it can be clearly seen that the body 12 defines lumina 14 and 18. While in FIG. 2, the lumina 14 and 18 are of equal lengths, it should be understood that the structure 10 will only have a self sealing capability along the length which is coextensive with lumen 18.

In a preferred embodiment, lumen 14 is of a sufficient internal diameter (ID) to allow blood flow therethrough. This means the ID of the lumen 14 will typically be between about 3 mm and about 24 mm depending on the application. Thickness of the common side wall 15 is generally in the range of between about 0.1 mm and 1.2 mm, depending upon the type of blood flow through the prosthesis. The thickness varies according to the type of pathway for which the prosthesis is used.

Figure 3A:
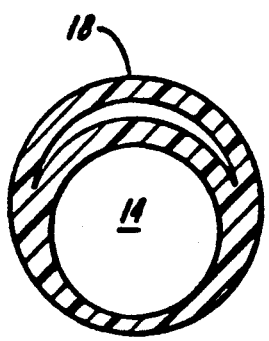
FIG. 3A and 3B are schematic cross-sectional views of other embodiments of the self-sealing vascular tubular structure of the invention.
Figure 3B:
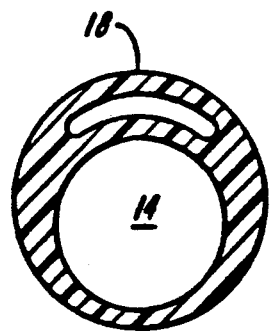

As shown, in FIGS. 3A and 3B, the cross-sectional configuration of the lumina designed in accordance with the invention may vary in size and shape depending upon the specific applications. In FIG. 3A, the secondary lumen 18 extends over approximately one-third of the circumference of the lumen 14. FIG. 3B shows a diminished relative size of the secondary lumen 18 with respect to the first lumen 14.

In a preferred embodiment the tube structures of the present invention are formed by extrusion of PTFE. Extrusion is performed using dies of predetermined shape of the type known in the art. FIG. 4 schematically shows an exemplary die 50, corresponding to the illustrated prosthesis of FIG. 1A. The dies may be manufactured from materials available and well known in the art.

Figure 4A:
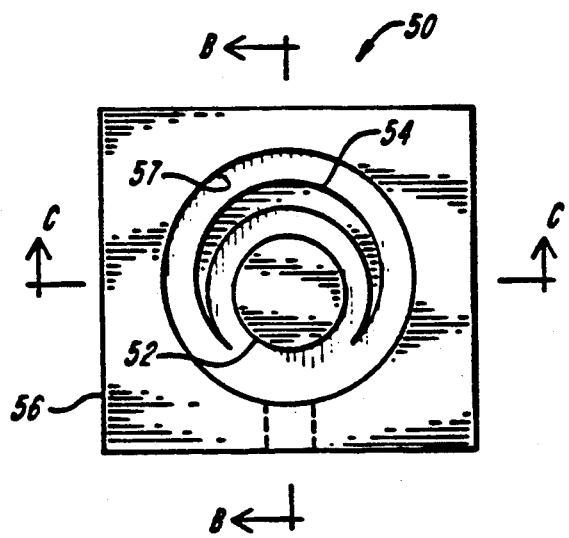
FIG. 4A, 4B and 4C show an exemplary die for manufacturing by extrusion the vascular tubular structure of the invention.
Figure 4C:
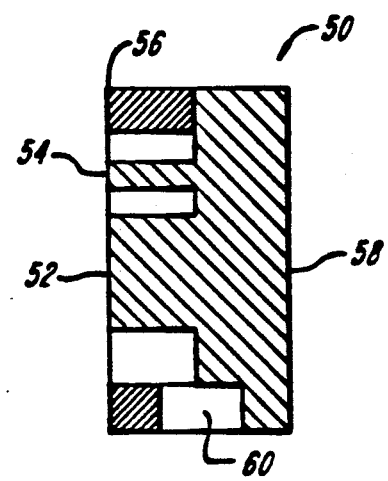
Figure 4B:
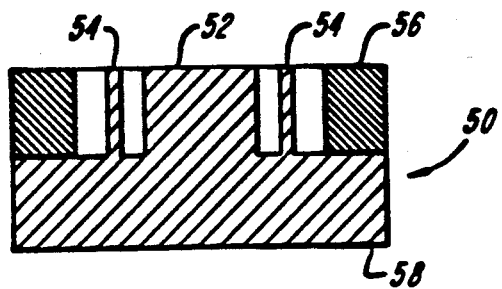

Generally, as illustrated in FIGS. 4A-4C, the die 50 consists of an upper plate 56 and a lower plate 58. The upper plate 56 defines a circular edge 57 corresponding to the other diameter of the tubular structure 10. The lower plate 58 includes a first hub 54 proximal to the hub 52 for forming a first lumen, such as lumen 14, and a second hub 54 proximal to the hub 52 for forming a secondary lumen, such as lumen 18. The specific spacing of the first hub 52 from the second hub 54 depends upon the specific desired prosthesis configuration. This spacing will dictate, for example, the thickness of the common side wall 15. As best shown in cross-section in FIG. 4C, the die 50 typically includes a channel 60 for introduction of PTFE paste, of the like, under pressure for extrusion. The manufacture of such dies is understood to be well known in the art.

After the PTFE resin is formed, such as by extrusion as discussed above, it is stretched and/or expanded and then sintered while being held in the stretched and/or expanded state. Stretching refers to elongation of formed resin while expansion refers to enlargement of the formed resin perpendicularly to its longitudinal axis. The rate of stretching and the stretch ratio affect the porosity of the finished product in a predictable manner allowing a prosthetic device to be produced having a specified porosity. The rate of stretching refers to the percentage of elongation per second that the resin is stretched while the stretch ratio refers to the relationship between the final length of the stretched resin and the initial length of the stretched resin. For example, stretching an extruded PTFE tube at a stretch ratio of two to one and a stretch rate of sixty results in a porosity of approximately fourty. This porosity is unitless and is determined as set forth on page eighty-four of the American Society For Testing of Materials' Special Technical Publication Number 898. So, for example, based on stretch ratios ranging from two to one, to six to one, a stretch rate of sixty percent per second yields a porosity of between approximately fourty and approximately ninety, a stretch rate of one hundred and fourty percent per second yields a porosity of between approximately sixty and approximately eighty-five, and a stretch rate of nine hundred percent per second yields a porosity of between approximately sixty-five and approximately eighty-five.

In addition to the porosity, the geometry of the node and fibril network of PTFE can be controlled during stretching and expansion. In the case of uniaxial stretching, that is, elongation of the formed PTFE resin along the direction of extrusion, the nodes are elongated causing the longer axis of each node to be oriented perpendicularly to the direction of stretch. Accordingly, the fibrils are oriented parallel to the direction of stretch. Biaxial stretching, additionally includes expanding the PTFE resin in the radial direction and can be utilized to produce a prosthetic device having a composite porosity. As in uniaxial stretching, the rate and ratio of radial expansion affects the resulting porosity of the prosthetic device.

In one embodiment, the apparatus of the present invention includes co-extruded plural lumina, as shown in FIG. 1, the secondary lumen 18 of which extends substantially along the entire length of the first lumen 14'. In another embodiment of the invention 10', as shown in FIG. 5, a secondary lumen 18' extends along only a portion of the tubular structure 10' which includes the secondary lumen 18 provides a self-sealing feature.

Figure 5A:
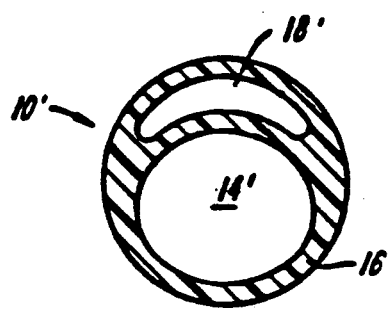
FIGS. 5 and 5A are schematic views of still another embodiment of the self-sealing vascular tubular structure of the invention.
Figure 5:
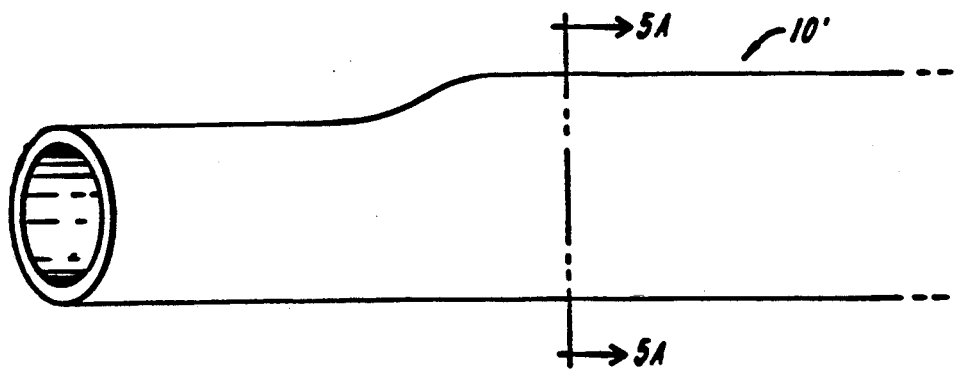

Otherwise, illustrated tubular structure 10' of FIG. 5 is structurally similar to the tubular structure 10 shown in FIG. 1. As shown in cross-section in FIG. 5A, the portion of the structure 10' which includes a secondary lumen includes a common side wall 15' between the secondary lumen 18' and the main lumen 14'. In the is illustrated embodiment, however, the secondary lumen 18' only extends along a predetermined portion of the structure 10'.

The embodiment shown of FIG. 5 can be manufactured in a manner similar to that described above. The extrusion die for forming the partially-extending lumen may be modified in a manner known to those skilled in the art. For example, the die used in the extrusion of this embodiment of the invention may include a shunt which allows selective opening and closing of an aperture for coextruding a secondary lumen.

The method of the invention comprises utilizing the present self-sealing graft device to replace or augment part of AV pathway in an individual. In the method, a surgeon or other qualified person surgically exposes the desired region for introduction of the graft of the of the invention. The desired site may be an area of occlusion of weakness in the patient's arteriovascular system, for example. An interruption of the patient's blood flow is performed, and the device is surgically implanted and sutured or otherwise secured in place so that blood flow is established through the primary lumen. Once the graft is in place, the bloodstream can be accessed by a cannula, intravenous needle or the like through the secondary lumen. When the cannula or needle is withdrawn, the elastomer on the secondary lumen will compress thereby prevent blood from escaping from the area of access.

The invention may be embodied in other specific forms without departing from the spirit of essential characteristics thereof. The present embodiments are therefor to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A self-sealing implantable prosthetic device for connection to a fluid flow pathway of a patient, the device comprising
   a. an implantable body of unitary construction adapted for attachment to said fluid flow pathway, said body defining a primary lumen for accommodating fluid flow therethrough and a secondary lumen sharing a common side wall with said primary lumen, each of the lumina being bounded by a single, continuous surface provided by the body; and
   b. a non-biodegradable self-sealing elastomeric material disposed in said secondary lumen.

2. The device of claim 1, wherein said primary lumen is longer than said secondary lumen.

3. The device of claim 1, wherein said body consists of a material selected from the group consisting of: polyester fibers, polyurethane, polysiloxane polymers, and polytetrafluoroethylene.

4. The device of claim 3, wherein said polytetrafluoroethylene is selected from the group consisting of, expanded polytetrafluoroethylene, stretched polytetrafluoroethylene, and stretched and expanded polytetrafluoroethylene.

5. The device of claim 1, wherein said body consists of a copolymeric material.

6. A self-sealing implantable vascular graft for connection to a blood vessel of a patient, the graft comprising
   a. an implantable body of unitary construction adapted for attachment to a blood vessel of a patient, said body defining a primary lumen for accommodating blood flow therethrough and a secondary lumen sharing a common side wall with said primary lumen, each of the lumina being bounded by a single continuous surface provided by the body, and
   b. a non-biodegradable self-sealing elastomeric material disposed in said secondary lumen.

7. The graft of claim 6, wherein said primary lumen is longer than said secondary lumen.

8. The graft of claim 6, wherein said body consists of a material selected from the group consisting of: polyester fibers, polyurethane, polysiloxane polymers, and polytetrafluoroethylene.

9. The device of claim 6, wherein said polytetrafluoroethylene is selected from the group consisting of, expanded polytetrafluoroethylene, stretched polytetrafluoroethylene, and stretched and expanded polytetrafluoroethylene.

10. The device of claim 6, wherein said body consists of a copolymeric material.

11. A method for accessing a patient's vascular system comprising the steps of:
    a. providing a vascular graft formed of an implantable body of unitary construction adapted for attachment to a blood vessel of the patient, the body defining a primary lumen for accommodating fluid flow therethrough and a secondary lumen sharing a common side wall with the primary lumen, each of the lumina being bounded by a single, continuous surface provided by the body, the graft further including a non-biodegradable self-sealing elastomeric material disposed in the secondary lumen;
    b. connecting the vascular graft to a blood vessel of the patient; and
    c. accessing the patient's vascular system by passing a cannula through said secondary lumen, said common side wall, and into said primary lumen.

* * * * *